(12) United States Patent
Hofmann et al.

(10) Patent No.: US 11,536,711 B2
(45) Date of Patent: Dec. 27, 2022

(54) MEASURING CARTRIDGE FOR MEASURING A LIQUID SAMPLE

(71) Applicant: EXIAS Medical GmbH, Graz (AT)

(72) Inventors: Wolfgang Hofmann, Graz (AT); Wolf-Dietrich Steinböck, Graz (AT); Josef Hindinger, Graz (AT)

(73) Assignee: EXIAS MEDICAL GMBH, Graz (AT)

( * ) Notice: Subject to any disclaimer, the term of this patent is extended or adjusted under 35 U.S.C. 154(b) by 551 days.

(21) Appl. No.: 16/665,868

(22) Filed: Oct. 28, 2019

(65) Prior Publication Data

US 2020/0132667 A1 Apr. 30, 2020

(30) Foreign Application Priority Data

Oct. 29, 2018 (DE) .................... 10 2018 126 952.8

(51) Int. Cl.
*G01N 1/00* (2006.01)
*G01N 33/49* (2006.01)
(Continued)

(52) U.S. Cl.
CPC ......... *G01N 33/4915* (2013.01); *C12M 23/42* (2013.01); *G01N 1/10* (2013.01);
(Continued)

(58) Field of Classification Search
CPC .... G01N 33/4915; G01N 1/10; G01N 21/274; G01N 27/4163; G01N 27/4165;
(Continued)

(56) References Cited

U.S. PATENT DOCUMENTS

| 5,948,366 A | 9/1999 | Rüther |
| 6,136,607 A | 10/2000 | Conlon et al. |

(Continued)

FOREIGN PATENT DOCUMENTS

| CN | 104380103 | * 1/2015 |
| CN | 104956222 | * 10/2018 |

(Continued)

OTHER PUBLICATIONS

European Office action for Patent Application No. 19205229.8, dated Mar. 31, 2022, 5 pages.
(Continued)

*Primary Examiner* — Robert R Raevis
(74) *Attorney, Agent, or Firm* — Lewis Roca Rothgerber Christie LLP (57) ABSTRACT

It is provided a measuring cartridge (1) for measuring at least one constituent of a liquid sample, in particular blood, and for performing quality control, the cartridge comprising: a casing (3) insertable into a reception opening (51) of a measuring instrument (50), the casing (3) at least partly surrounding an inner space (5); wherein the inner space contains: a measurement cell (7) comprising a reception space (9) for the sample and at least one sensor area (11) with which the sample is in contact when loaded into the reception space (9); plural quality control containers (13a, 13b, 13c) for respectively holding different quality control solutions (15a, 15b, 15c); a solution routing system (17) adapted to selectively route one of the quality control solutions (15a, 15b, 15c) from the respective quality control container (13a, 13b, 13c) into the reception space (9) of the measurement cell (7).

19 Claims, 3 Drawing Sheets

(51) Int. Cl.
*C12M 3/00* (2006.01)
*G01N 1/10* (2006.01)
*G01N 35/00* (2006.01)
*B01L 3/00* (2006.01)

(52) U.S. Cl.
CPC ........ *G01N 35/00613* (2013.01); *B01L 3/508* (2013.01); *B01L 2200/026* (2013.01)

(58) Field of Classification Search
CPC ......... G01N 27/4175; G01N 35/00594; G01N 2201/1288; G01N 35/00603; G01N 35/00613; G01N 35/00623; C12M 23/42; B01L 3/508; B01L 2200/026; B01L 3/502738; B01L 2200/148; B01L 2300/0627; B01L 2300/0816; B01L 2300/0867; B01L 2400/0475; B01L 2400/0644; B01L 3/502715
USPC .................. 73/64.56, 1.02, 53.01, 61.41, 73/61.43–61.49, 864.73, 864.81; 324/425, 438, 130; 422/68.1, 422/82.01–82.13; 436/8; 356/243.1–243.8
See application file for complete search history.

(56) References Cited

U.S. PATENT DOCUMENTS

| | | | |
|---|---|---|---|
| 7,022,219 B2 | 4/2006 | Mansouri et al. | |
| 7,338,802 B2 | 3/2008 | Frischauf et al. | |
| 8,506,778 B2* | 8/2013 | Lauks | B01L 3/502738 422/503 |
| 11,047,845 B1* | 6/2021 | Barry, Jr. | G01N 15/14 |
| 2003/0224523 A1* | 12/2003 | Thornberg | B01L 3/502738 422/63 |
| 2005/0249634 A1 | 11/2005 | Devlin | |
| 2009/0176314 A1 | 7/2009 | Steinboeck et al. | |
| 2013/0136657 A1* | 5/2013 | Hofmann | B05D 5/00 422/68.1 |
| 2013/0142709 A1* | 6/2013 | Lin | G01N 27/4163 422/537 |
| 2013/0244241 A1 | 9/2013 | Carrera Fabra et al. | |
| 2014/0296089 A1* | 10/2014 | Holmes | B01L 3/50855 435/7.1 |
| 2016/0356801 A1* | 12/2016 | Glavina | G16H 10/40 |
| 2017/0065970 A1 | 3/2017 | Nauschnegg | |
| 2018/0292346 A1* | 10/2018 | Collison | G01N 27/42 |

FOREIGN PATENT DOCUMENTS

| | | | |
|---|---|---|---|
| WO | 94/19683 | * | 9/1994 |
| WO | 97/43639 | A1 | 11/1997 |
| WO | 2004/040284 | A1 | 5/2004 |
| WO | 2005085855 | A2 | 9/2005 |
| WO | WO 2015/035256 | A2 | 3/2015 |

OTHER PUBLICATIONS

European Search Report issued in parallel European Application No. 19205229.8-1001, dated Apr. 1, 2020, 10 pages.
Nichols et al, "Evaluation of $QC^3$: The Automatic Quality Control System on the ABL80 Flex"; Point of Care; vol. 7; No. 2 54-59; Jun. 2008 [Abstract].
QC—Lösung von Fa Nova; "BioProfile pHOx Analyzer", Nov. 29, 2017; http://www.novabio.us/phox/#, 1pg.
Siemens; "RAPIDPoint 500 Systems"; Nov. 2017; https://www.healthcare.siemens.com/point-of-care-testinq/blood-gas/blood-gas-systems/rapidpoint-500-systems; 1pg.

* cited by examiner

MEASURING CARTRIDGE FOR MEASURING A LIQUID SAMPLE

CROSS-REFERENCE TO RELATED APPLICATION(S)

This application claims priority to and the benefit of German Patent Application No. 10 2018 126 952.8, filed on Oct. 29, 2018, the entire contents of which are incorporated herein by reference.

FIELD OF THE INVENTION

The present invention relates to a measuring cartridge for measuring at least one constituent of a liquid sample and performing quality control, relates to a measuring system and further relates to a method for measuring at least one constituent of a liquid sample and performing quality control.

BACKGROUND

For diagnostic purposes, a liquid sample, such as a blood sample, may be examined, in order to determine respective concentrations of different constituents, such as blood gases, electrolytes and metabolites. These kinds of measurements may be performed for diagnostic and/or therapeutic purposes. For example, a partial pressure of oxygen, a partial pressure of carbon dioxide, a pH or an electrolyte concentration, such as of calcium, sodium, potassium and/or chloride ions may be measured.

In order to ensure accuracy of the measurement results, such as partial pressures and/or concentration of different gases and/or electrolytes, quality control must be performed from time to time or in a regular manner after particular time intervals. Thereby, quality control has conventionally been performed in that solutions with known analyte concentrations are measured and the measurement results are compared to target ranges. Depending on whether the measurement results comply with the known concentrations or not, re-calibration of the measurement system and/or replacement and/or repair of components of the measurement system may be required.

Conventionally, quality control solutions are contained in sealed ampules. The user has to open the ampule immediately before the measurement and needs to apply the quality control solution. The ampules may be arranged in a rack and may for example be placed in a carousel. The conventionally used ampules are relatively expensive, since one ampule may only be utilized for a single measurement. Furthermore, the user has to manipulate the ampules manually, requiring corresponding skills. Conventionally, so-called quality control packs which may comprises plural pouches have been proposed which may be attached to a measuring apparatus and which may contain several quality control solutions.

The conventionally known systems have a number of disadvantages, in particular the difficulties and/or inconvenience of usage, the relatively high price and high number of required equipment parts to handle.

Thus, there may be a need for a measuring cartridge for measuring at least one constituent of a liquid sample and performing quality control, there may be a need for a corresponding method and there may be a need for a measuring system, wherein quality control may be performed orthogonal and independent of calibration in a simplified manner, without needing user intervention, and providing easy handling.

SUMMARY OF THE INVENTION

The need is satisfied by the subject-matter of the independent claims. The dependent claims specify particular embodiments of the present invention.

According to an embodiment of the present invention it is provided a measuring cartridge for measuring at least one constituent of a liquid sample, in particular blood, and for performing quality control, the cartridge comprising: a casing insertable into a reception opening of a measuring instrument, the casing at least partly surrounding an inner space; wherein the inner space contains: a measurement cell comprising a reception space for the sample and at least one sensor area with which the sample is in contact when loaded into the reception space; plural quality control containers (for) respectively holding different quality control solutions; a solution routing system adapted to selectively route one of the quality control solutions from the respective quality control container into the reception space of the measurement cell.

The measuring cartridge, when inserted into the reception opening of the measuring instrument may, together with the measuring instrument, be enabled to perform a measurement of at least one constituent of the liquid sample. The measuring cartridge may be a component separate and independent of the measuring instrument. Thereby, the casing of the measuring cartridge may delimit the measuring cartridge. The casing may have an outer shape which is at least partly complementary to the shape of the reception opening of the measuring instrument. The measuring cartridge may be pushed into the reception opening along a straight path, e.g. until the measuring cartridge is latched and/or locked within the reception opening.

When the measuring cartridge is completely inserted into the reception opening, engagement portions of the measuring cartridge may engage with respective engagement portions of the reception opening of the measuring instrument, for example mechanical engagement portions and/or electrical engagement portions. Thereby, a mechanical and/or electrical connection between the measuring cartridge and the measuring instrument may be established. For example, the measuring cartridge may not by itself comprise an energy supply and/or may not comprise a pumping device. However, when inserted into the reception opening, the measuring instrument, for example having an energy supply and/or measurement data reception capability and/or pumping device, may supply components of the measuring cartridge with electric energy and/or receive measurement signals from the sensor area of the measurement cell (comprised in the measuring cartridge). Furthermore, the measuring instrument may comprise a peristaltic pump which may, when the measuring cartridge is completely inserted into the reception opening of the measuring instrument, come in contact with a flexible hose or tubing (comprised in the measuring cartridge) in order to establish a pumping action within tubing or hoses comprised in the measuring cartridge. Thus, the measuring cartridge and the measuring instrument may act in a synergistic manner together for enabling to perform a measurement.

During inserting the measuring cartridge into the reception opening, one or more outer, in particular plane, surface portions of the measuring cartridge may slide along or at one or more surface portions of the reception opening of the measuring instrument. Furthermore, one or more guiding trails may be provided at the measuring cartridge and/or the reception opening for aiding insertion of the measuring cartridge into the reception opening. Thus, the casing may not only harbour and protect components comprised in the measuring cartridge, but also may be adapted for aiding the insertion of the measuring cartridge into the reception opening.

Within the inner space partly surrounded by the casing, the measurement cell, at least the plural quality control containers and the solution routing system are arranged. The measurement cell may be configured as a flow-through cell allowing a sample to be measured to flow through the measurement cell, for example entering at an inlet and exiting at an outlet of the measurement cell. The sensor area may be exposed within the reception space such that the sample is in contact with the sensor area when present within the reception space. The measurement cell may in particular be a movable measurement cell, i.e. movable relative to other components of the measuring cartridge and in particular movable relative to the casing of the measuring cartridge. Providing a movable measurement cell may simplify sample loading, for example from a syringe, from a tube or a capillary, for example. In particular the path length to transport the sample and/or one of the quality control solutions into the measurement cell may be short.

The measurement cell may comprise a, in particular rigid and/or stiff, sample supply system, e.g. comprising a supply needle, which may be fixedly attached to the inlet of the measurement cell. Thereby, gas carry over observed in flexible tubes may be avoided. When the measurement cell is moved, for example translated and/or rotated, also the fixedly attached sample supply system may be moved. The sample supply system may for example comprise a hollow needle through which a sample may be introduced into the reception space of the measurement cell. Providing a movable measurement cell within the cartridge may be advantageous, since different sample source containers or external equipment may require different orientations and/or configurations of the sample supply system of the measurement cell, in order to be able to feed the sample from the external source into the reception space.

The sensor area(s) (e.g. comprising an electrode each) may for example be configured to measure the concentration of at least one ion, such as $K^+$, $Ca^{++}$, $Na^+$, $Cl^-$ and/or pH and/or partial pressures of $O_2$, $CO_2$ and/or concentrations of glucose, lactate, urea, creatinine or the like. In particular, the measurement cell may comprise (for example accessible within the reception space) plural separate sensor areas, for example for each analyte to be examined at least one separate respective sensitive area. In particular, the sensitive areas may be arranged side by side along a longitudinal direction (e.g. flow direction of the sample) of the reception space.

The sensor area, in particular together with measurement signal processing portions arranged within the measuring instrument, may be adapted to perform potentiometric and/or amperometric measurements and/or conductometric measurements, for example measurements of electrical potentials and/or electrical currents and/or electric impedances. As measurement result, concentration of different analytes may be determined and/or the values of partial pressures of different gases within the sample may be determined and/or the volumetric amount of blood cells may be determined.

The reception space of the measurement cell may for example be configured as a channel or a tunnel having a longitudinal direction corresponding to a flow direction during supply of the sample into the reception space and/or also during the measurement. The measurement cell may substantially be constructed from two portions each of which may partially provide restricting surfaces for the reception space. One of the portions may comprise the one or more sensor areas.

The different quality control solutions may comprise target constituents in physiologically expected concentrations, for example of a healthy patient and a pathological or sick patient. Each of the quality control solutions may comprise a mixture of different target constituents in a particular concentration. The solutions may in particular be aqueous solutions. When the plural quality control containers are arranged within the inner space of the measuring cartridge, it may not be required anymore to manually load a quality control solution from for example an ampule into the measurement cell, thereby simplifying the usage of the measuring cartridge and in particular simplifying quality control measurements. The different quality control solutions must be different from calibration solutions which may be utilized for calibration of the measurement system. In particular, a calibration solution may in contrast contain target constituents in non-physiological concentrations.

The solution routing system may comprise one or more components, such as a distribution system and/or tubing(s) and/or hose(s) and/or valve(s). In particular, the quality control containers may be provided with a respective valve which may be open(ed), when this respective quality control solution is to be supplied to the measurement cell.

When plural different quality control solutions are arranged within the measuring cartridge, a thorough quality control may be performed, in order to in particular reliably distinguish a healthy condition of the sample from a pathological condition of the sample. Thereby, a reliable quality control may be performed.

According to an embodiment of the present invention, the different quality control solutions contain mixtures of plural target constituents, in particular $H^+$, $Na^+$, $K^+$, $Ca^{2+}$, $Cl^{2-}$, in different concentrations.

The target constituents may represent species which are also measured for an actual sample, such as a human sample for e.g. a diagnostic purpose. Thus, the target constituents may correspond to clinically interesting species or constituents of a clinical sample. The different concentrations of the plural target constituents are predetermined and known in advance. Measuring the different quality control solutions should result in measurement results of predetermined value(s) or of predetermined value range(s). If measuring the plural different quality control solutions does not result in the determination of the concentrations of the target constituents in the predetermined ranges, it may be indicated, that there is a problem and/or fault in one or more components of the entire measurement system comprising the measuring cartridge and/or the measuring instrument. For example, the sensor area of the measurement cell may be faulty and/or the reception space may be contaminated or one or more of the tubings may be contaminated or deteriorated. Thus, if the measurement results do not comply with expected results, the entire measuring cartridge may be replaced by a new measuring cartridge. In other cases, re-calibrations may be performed, for example using one or more calibration solutions which may also be comprised within calibration solution containers within the measuring cartridge.

According to an embodiment of the present invention, the different concentrations of the plural target constituents within the different quality control containers are selected to at least correspond to a physiologically normal range, to a pathologically elevated range, and to a pathologically lowered range. Conventionally, quality control concepts have adopted a three level system. Thereby, the analyte concentrations from the physiologically normal range as well as pathologically increased and pathological lowered ranges are simulated. Thus, a clinically relevant range may be covered by the different quality control solutions.

According to embodiments of the present invention, the target constituents may comprise pH, Na, K, Ca, Cl and in the levels 1, 2 and 3 as given in Table 1.

TABLE 1

|  | pH | Na | K | Ca | Cl |
|---|---|---|---|---|---|
| Level 1 | ↓ | ↓ | ↓ | ↑ | ↓ |
| Level 2 | "normal" | "normal" | "normal" | "normal" | "normal" |
| Level 3 | ↑ | ↑ | ↑ | ↓ | ↑ |

The "arrow down" indicates a pathologically lower concentration range, the "arrow up" represents a pathologically increased concentration and "normal" indicates a physiologically normal range, i.e. a healthy or a range considered as healthy.

The following concentrations of the target constituents may be present, in particular within three different quality control solutions, as given in Table 2.

TABLE 2

|  | pH [1] | Na [mmol/l] | K [mmol/l] | iCa* [mmol/l] | Cl [mmol/l] |
|---|---|---|---|---|---|
| Level 1 | 7.15 | 115 | 3.0 | 1.7 | 80 |
| Level 2 | 7.38 | 145 | 4.5 | 1.2 | 105 |
| Level 3 | 7.60 | 165 | 6.2 | 0.70 | 125 |

In other embodiments of the present invention, less or more target constituents may be comprised within the different quality control solutions and they may have concentrations different than indicated in the above tables 1 and 2. iCa is the as ionized indicated calcium (free, not masked), in contrast to the total calcium (tCa), this value is always higher. Thereby, conventionally applied quality control solutions may be supported.

According to an embodiment of the present invention, at least one of the plural quality control containers comprises a pouch, in particular made of plastic, wherein at least one of the plural quality control containers in particular has a volumetric capacity of between 1 ml and 250 ml, in particular between 10 ml and 50 ml.

In particular, all plural quality control containers may be configured as a pouch or a bag. Thereby, the containers may be manufactured in a cost-effective way. Each of the containers may comprise for example one or more caps or closures that may be configured to close openings, in particular one for withdrawing the respective quality control solution and another one to ventilate the interior of the respective container.

The entire measuring cartridge may be an component which is to be disposed after a particular number of measurements have been taken, for example after 50 to 1000 measurements have been taken. The user may then acquire a new measuring cartridge having installed therein all quality control containers including the different quality control solutions. The measuring cartridge may then be ready to use without requiring to install additional quality control solutions.

The plural quality control containers may, according to an embodiment of the present invention, arranged side by side within receptacles within the inner space of the measuring cartridge. The receptacles may for example be configured as cuboid compartments or slots. Thereby, it may be ensured that the different quality control containers have approximately a same or similar distance to the reception space of the measurement cell, in particular with respect to the tubing length between the respective container and the measurement cell. Thereby, same or at least similar measurement conditions may prevail when measuring the different quality control solutions.

According to an embodiment of the present invention, the solution routing system comprises: a rotary distributor having plural inlets connected to at least the quality control containers and having at least one outlet connected to an inlet of the measurement cell, the rotary distributor being adapted to allow solution communication between a selected inlet and the outlet. The rotary distributor may comprise, in particular in the rotatable portion of the rotary distributor, a guiding channel or guiding tunnel for guiding a solution or air connected to a particular inlet to the outlet of the rotary distributor. The particular inlet may be selected by appropriately rotating the rotatable portion of the rotary distributor such that the guiding channel ends at the particular inlet. The outlet may be provided in a central portion of the rotary distributor, in particular at a portion where the guiding channel or guiding tube ends.

The rotary distributor may allow also, e.g. via an air inlet, intake of air to e.g. form an air bubble for separating fluid package from different inlets for avoiding mixing of different solutions.

When a particular inlet is selected, the quality control solution of that container is pumped into the measurement cell which is connected to the selected inlet of the rotary distributor. The quality control solution then flows from the respective quality control solution container via a tubing to the selected inlet from there through the guiding tube or guiding channel within the rotary distributor, through the outlet of the rotary distributor and to the inlet of the measurement cell, to be loaded into the reception sample of the measurement cell.

The rotatable portion of the rotary distributor may be driven by an electrical motor comprised within the measuring instrument but not comprised within the measuring cartridge. Thereby, a particular driving motor within the measuring cartridge can be dispensed with, thereby simplifying the measuring cartridge.

According to an embodiment of the present invention, the rotary distributor comprises an engagement portion for engaging with a (e.g. first) gear wheel provided in the reception opening of the measuring instrument (when the measuring cartridge is inserted into the reception opening), allowing to selectively rotate a (rotatable) portion of the rotary distributor for establishing solution communication between a selected inlet and the outlet of the rotary distributor.

By engaging the engagement portion of the rotary distributor with a gear wheel provided in the reception opening of the measuring instrument, the rotary distributor may be controlled by an electric motor of the measuring instrument, in order to select a particular inlet (and thereby select a particular quality control container) via which the corresponding quality control solution enters the measurement cell. Therefore, the measuring instrument may e.g. have a look-up table stored, indicating which rotation state of the rotary distributor corresponds to which quality control solution to be in communication with the measurement cell.

According to an embodiment of the present invention, the inlet of the measurement cell comprises a, in particular straight, in particular fixedly connected, supply needle having an inner lumen, an end of the supply needle being reversibly connectable to the outlet of the rotary distributor. The supply needle may allow to easily load a sample into the reception space of the measurement cell. In particular, loading a sample from different source containers may be supported, such as from a tube, a syringe or a capillary for example. For loading the sample from different source containers, the measurement cell may be moved, in particular rotated, into an appropriate orientation and configuration. Thereby, not only quality control measurements are supported by the measuring cartridge but also the measurement of clinical sample. During a sample measurement as well as during a quality control measurement, however, the respective solution to be measured may flow through the supply needle in both cases. Thereby, same or at least similar conditions for the measurements are provided during quality control and actual sample measurement, thereby increasing the reliability of the measurement or the accuracy of the measurement.

The engagement portion of the rotary distributor may be arranged at a bottom side of the measuring cartridge. Correspondingly, the gear wheel in the reception opening which engages with the engagement portion of the rotary distributor may be arranged at a bottom surface of the reception opening of the measuring instrument. Thereby, it may in particular be enabled to arrange the rotary distributor in a horizontal orientation, such as the rotation axis of the rotatable portion is substantially in the vertical direction. Further, the guiding tunnel or guiding channel within the rotatable portion of the rotary distributor may substantially run in a horizontal direction, in particular irrespective which of the inlet is selected, i.e. irrespective which rotation position the rotatable portion of the rotary distributor adopts. Thereby, similar or even same measuring conditions may prevail irrespective which quality control solution is being measured.

According to an embodiment of the present invention, the measurement cell comprises an engagement portion for engaging with a (e.g. second) gear wheel accessible in the reception opening of the measuring instrument (when the measuring cartridge is inserted into the reception opening), allowing to move, in particular to at least rotate, the measurement cell, in particular allowing to remove the supply needle from the outlet of the rotary distributor and to expose the end of the needle through a sample supply opening within the casing of the cartridge for loading a sample to be examined.

The engagement portion of the measurement cell may be accessible at an outer side face of the measuring cartridge and may engage with the gear wheel (in particular also referred to as measurement cell gear wheel or second gear wheel) when the measuring cartridge is completely inserted into the reception opening of the measuring instrument. The measurement cell gear wheel (of the measuring instrument) may be arranged at a side surface of the reception opening of the measuring instrument. Thereby, a rotation axis of the measurement cell gear wheel (and therefore also a rotation axis of the measurement cell) may be arranged substantially in the horizontal plane. In particular, by rotating the measurement cell around the measurement cell gear wheel rotation axis (in particular horizontally arranged), the supply needle may be swivelled to protrude out of a loading opening (also referred to a sample supply opening) of the measuring cartridge such that the end of the needle is accessible to a user, in order to load, via the supply needle, a sample into the measurement cell. Thus, the rotation of the measurement cell may enable to adopt at least two states, namely a quality control or calibration state, in which the supply needle is inserted into the outlet of the rotary distributor, and a sample loading state in which the end of the supply needle is accessible from outside the measuring cartridge and in particular withdrawn from the outlet of the rotary distributor and in particular rotated with respect to the quality control and/or calibration state by an angle between 20° and 90° for example. When the measurement cell is in the loading state, the end of the supply needle may at least partially protrude from the measuring cartridge, in particular through the sample supply opening, such as to be accessible by a user.

According to an embodiment of the present invention, in a quality control operation mode, the selected quality control solution streams from the respective quality control container via the rotary distributor and via the supply needle into the reception space of the measurement cell and, in particular, via the outlet of the measurement cell out of the measurement cell. The supply path, in particular downstream the entry end of the supply needle, taken by the quality control solution may be similar or equal to the path taken by a real sample whose constituents are to be measured.

Thus, the supply needle forms part of the solution supply path in both cases, when an actual sample is to be loaded or when a quality control solution or a calibration solution is to be loaded into the measurement cell. Thereby, during quality control and/or calibration and/or actual sample measurement, substantially same or at least similar sample or solution supply conditions are enabled.

According to an embodiment of the present invention, the solution routing system comprises: plural tubes connected between the quality control containers and the inlets of the rotary distributor. The tubes may be flexible tubes, for example.

According to an embodiment of the present invention, the cartridge further comprises at least one calibration container for holding a calibration solution for calibrating the sensor of the measurement cell, the calibration container being connected to the rotary distributor. In particular, several calibration containers holding several different calibration solutions may be connected to the rotary distributor. The calibration solutions may comprise the target constituents in non-physiological concentrations, in contrast to the concentrations of the target constituents comprised within the quality control solutions. Measuring one or more of the calibration solutions may allow adjusting one or more parameters, such as a measurement gain factor, of the one or more sensor areas. Measurement of the calibration solution or solutions may enable to establish a reference curve relating a concentration of one or more constituents to a measurement signal strength, for example. When also the calibration solutions are comprised within the cartridge, no further additional calibration solutions need to be provided from outside, thereby simplifying the usage of the cartridge.

According to an embodiment of the present invention, the measurement cell is configured as a flow-through measurement cell and further comprises an outlet, wherein the inner space further contains: a flexible waste tube connected to the outlet of the measurement cell and arranged to engage with a driving wheel of a peristaltic pump of the measuring instrument when inserted into the opening of the measuring instrument; in particular a waste container connected to an end of the waste tube for collecting liquids flown through and measured within the measurement cell.

During operation, in particular all tubes including the waste tube may be filled with aqueous solution without air bubbles. When the flexible waste tube contacts and engages with a driving wheel of the peristaltic pump of the measuring instrument, solution comprised in the flexible waste tube may be displaced and solution contained within the measurement cell and tubing beyond the measurement cell will be sucked, thereby establishing a flow within connected tubings and components inside the measuring cartridge. Thus, the measuring cartridge may not comprise a peristaltic pump, but only a mechanical interface allowing the driving wheel of the peristaltic pump of the measuring instrument to cause flow of solution comprised in the flexible waste tube. In other embodiments, the peristaltic pump of the measuring instrument may be brought in contact with one or more other portions of the tubing system comprised within the measuring cartridge, not necessarily being the flexible waste tube.

When also the waste container is comprised in the measuring cartridge, the measuring cartridge may not need to require any further liquid connection and may in particular collect all measured solutions in the waste container. Thereby, contamination to outside portions may be avoided.

According to an embodiment of the present invention, the cartridge further comprises plural electrical contact areas accessible from outside the casing adapted to at least electrically contact the sensor of the measuring cell with circuitry of the measuring instrument. The measuring cell, in particular the at least one sensor area, may provide analogous and/or digital signals which may be output at the plural electrical contact areas and may thereby be supplyable to the circuitry of the measuring instrument. In particular, the electrical contact areas may be provided in a top portion of the measuring cartridge, thereby reducing contact to liquids. In other embodiments, the measurement signals may be transmitted wirelessly from the measuring cartridge to the measuring instrument.

According to an embodiment it is provided a measuring system, comprising a measuring instrument having an reception opening; and a measuring cartridge according to one of the preceding embodiments insertable, in particular inserted, into the reception opening, the measuring instrument being adapted to receive measurement signals from the sensor of the measurement cell, the measuring instrument being adapted to selectively: adopt a quality control operation mode, in which a quality control solution from one of the quality control containers is supplied into the reception space of the measurement cell; or adopt a sample measurement mode, in which a sample is supplied into the reception space of the measurement cell.

When the measuring cartridge is completely inserted into the measuring instrument, in particular into the reception opening, the measurement system is ready to perform a measurement of an actual sample of perform quality control. The measurement system may further be adapted to selectively adopt a calibration operation mode, in which a calibration solution from one or more of calibration containers is supplied into the reception space of the measurement cell.

Providing a measurement system with the measuring cartridge may enable to meet hygiene requirements more easily in a convenient manner. For example, when a used measuring cartridge is contaminated, e.g. by microbes or pathogenic germs, replacement of merely this measuring cartridge with a new one suffices for ensuring clean equipment without the requirement to additionally also replace a separate quality control cartridge as was used in the prior art.

It should be understood, that features, individually or in any combination, described, explained or provided for a measuring cartridge for measuring at least one constituent of a liquid sample and performing quality control are also, individually or in any combination, applicable to a method for measuring at least one constituent of a liquid sample, and performing quality control according to embodiments of the present invention and vice versa.

According to an embodiment of the present invention it is provided a method for measuring at least one constituent of a liquid sample, in particular blood, and performing quality control, the method comprising: using a measuring cartridge with a casing inserted into a reception opening of a measuring instrument, the casing at least partly surrounding an inner space; loading a sample into a reception space of a measurement cell arranged within the inner space; contacting at least one sensor area of the measurement cell with the sample; routing one of plural quality control solutions from a respective quality control container arranged within the inner space into the reception space of the measurement cell.

The method may in particular be performed by a measurement system according to an embodiment of the present invention. Thereby, in particular, a measuring cartridge according to an embodiment of the present invention may be utilized. Advantageously, the measuring cartridge has all parts and equipment included that are necessary to perform sample measurements as well as quality control procedures, no further components need to be handled.

The operation of the measurement system may be controlled for example by a control area or control display provided at the measuring instrument. In particular, the measuring instrument may control the gear wheels and may also control the peristaltic pump and may receive the measurement signals from the measurement cell within the measuring cartridge. Furthermore, the measuring instrument may count the number of measurements which have been performed by the same measuring cartridge. After a particular number of measurements and/or after a particular time interval, the measuring instrument may indicate that a quality control operation and/or a calibration operation is to be adopted. During the quality control operation and/or calibration operation one or more of the quality control solutions contained within the measuring cartridge may be measured in the measurement cell for generating quality control measurement values.

The measuring instrument may further comprise an electronic storage for storing the quality control measurement values and having stored therein reference values or target values for the different quality control solutions. The quality control measurement values may then be compared with the target values within the measuring instrument. Further, a history report of past quality control measurement values in relation to the target values may be generated and displayed thereby supporting auditing.

The aspects defined above and further aspects of the present invention are apparent from the examples of embodiment to be described hereinafter and are explained with reference to the examples of embodiment. The invention will be described in more detail hereinafter with reference to examples of embodiment but to which the invention is not limited.

DETAILED DESCRIPTION OF EMBODIMENTS

Figure 1:
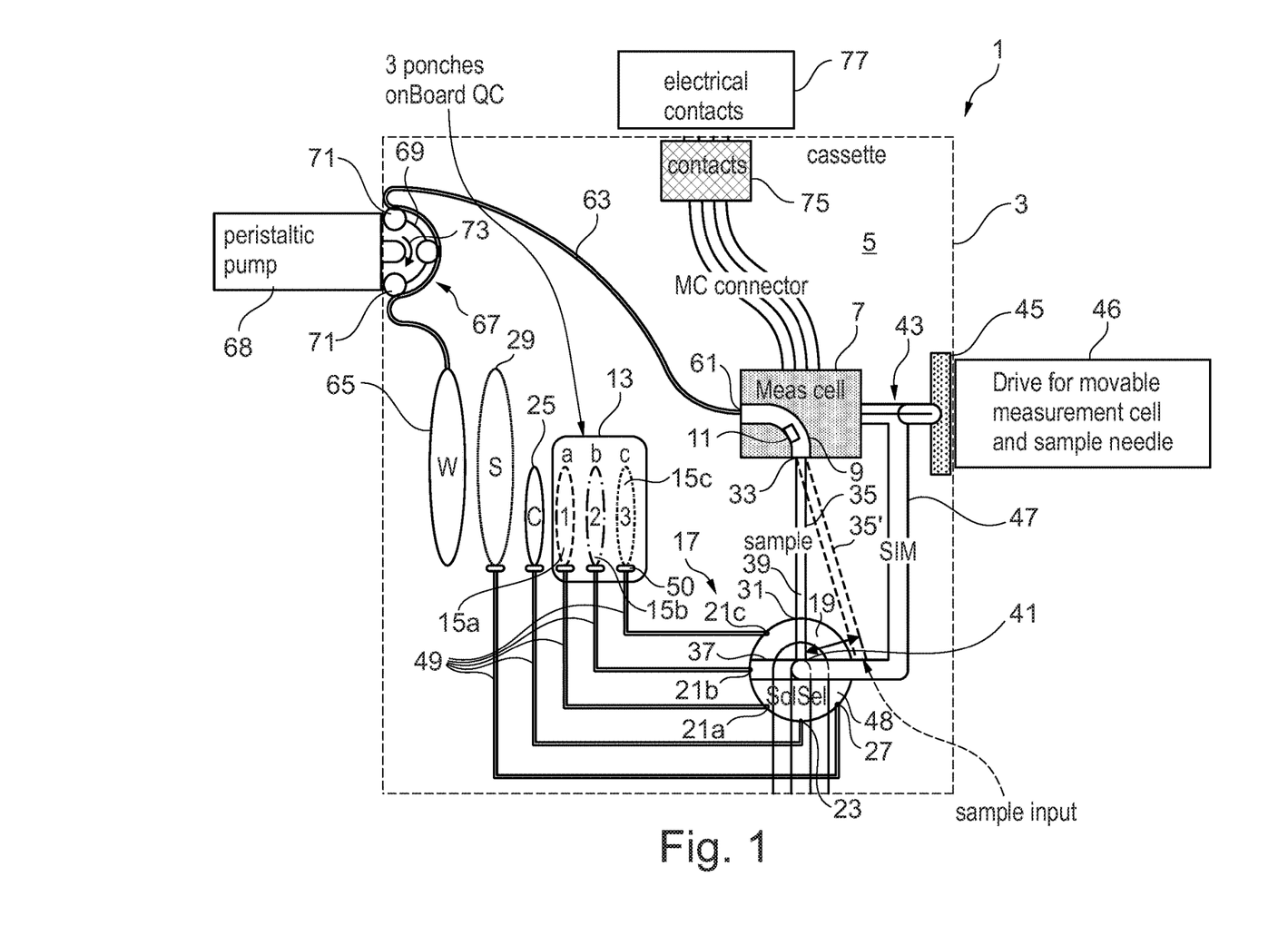
FIG. 1 schematically illustrates a measuring cartridge according to an embodiment of the present invention.

The measuring cartridge 1 schematically illustrated in FIG. 1 according to an embodiment of the present invention, for measuring at least one constituent of a liquid sample and for performing quality control, comprises an only illustrated casing 3 which is insertable into a not illustrated reception opening of a measuring instrument, the casing 3 at least partly surrounding an inner space 5. The inner space 5 comprises a movable measurement cell 7 comprising a not in detail illustrated reception space 9 for the sample and at least one sensor area 11 with which the sample is in contact when loaded into the reception space 9.

The inner space 5 further comprises plural quality control containers 13, in particular the quality control containers 13a, 13b, 13c for respectively holding different quality control solutions 15a, 15b, 15c, respectively. The inner space 5 further contains a solution routing system 17 which is adapted to selectively route one of the quality control solutions 15a,b,c from the respective quality control container 13a,b,c, respectively, into the reception space 9 of the measurement cell 7.

The quality control solutions 15a,b,c each comprise mixtures of plural target constituents in different concentrations. In particular, the different concentrations of the plural target constituents are selected to at least correspond to a physiologically normal range ("normal"), to a pathologically elevated range ("arrow up") and to a pathologically lowered range ("arrow down"). The quality control containers 13a, 13b, 13c are in particular configured as a pouch or a bag, in particular plastic bag. The capacity of the quality control containers may be sufficient for performing quality control measurements until the measuring cartridge 1 has been used so often that it needs to be discarded and replaced by a new measuring cartridge.

The solution routing system 17 comprises a rotary distributor 19 having plural inlets 21a, 21b, 21c connected to the different quality control containers 13a, 13b, 13c, respectively. Furthermore, the rotary distributor 19 comprises an inlet 23 connected to a calibration container 25 which holds a calibration solution for calibrating in particular the at least one sensor area 11 of the measurement cell 7. The rotary distributor 19 further comprises an inlet 27 which is connected to a calibration "standby" container 29 which may, during standby, perform a calibration procedure and/or washing procedure.

The rotary distributor further comprises an outlet 31 which is connected to an inlet 33 of the measurement cell via a supply needle 35 which is fixedly attached to the measurement cell 7. The rotary distributor is adapted to allow solution communication between a selected inlet of the inlets 21a, 21b, 21c, 23, 27 and the outlet 31. For this purpose, the rotary distributor comprises a rotatable portion comprising a guiding channel 37 which orientation is changed due to the rotation of the rotatable portion and which, selectively, connects one of the inlets with the outlet 31 of the rotary distributor 19.

Figure 3:
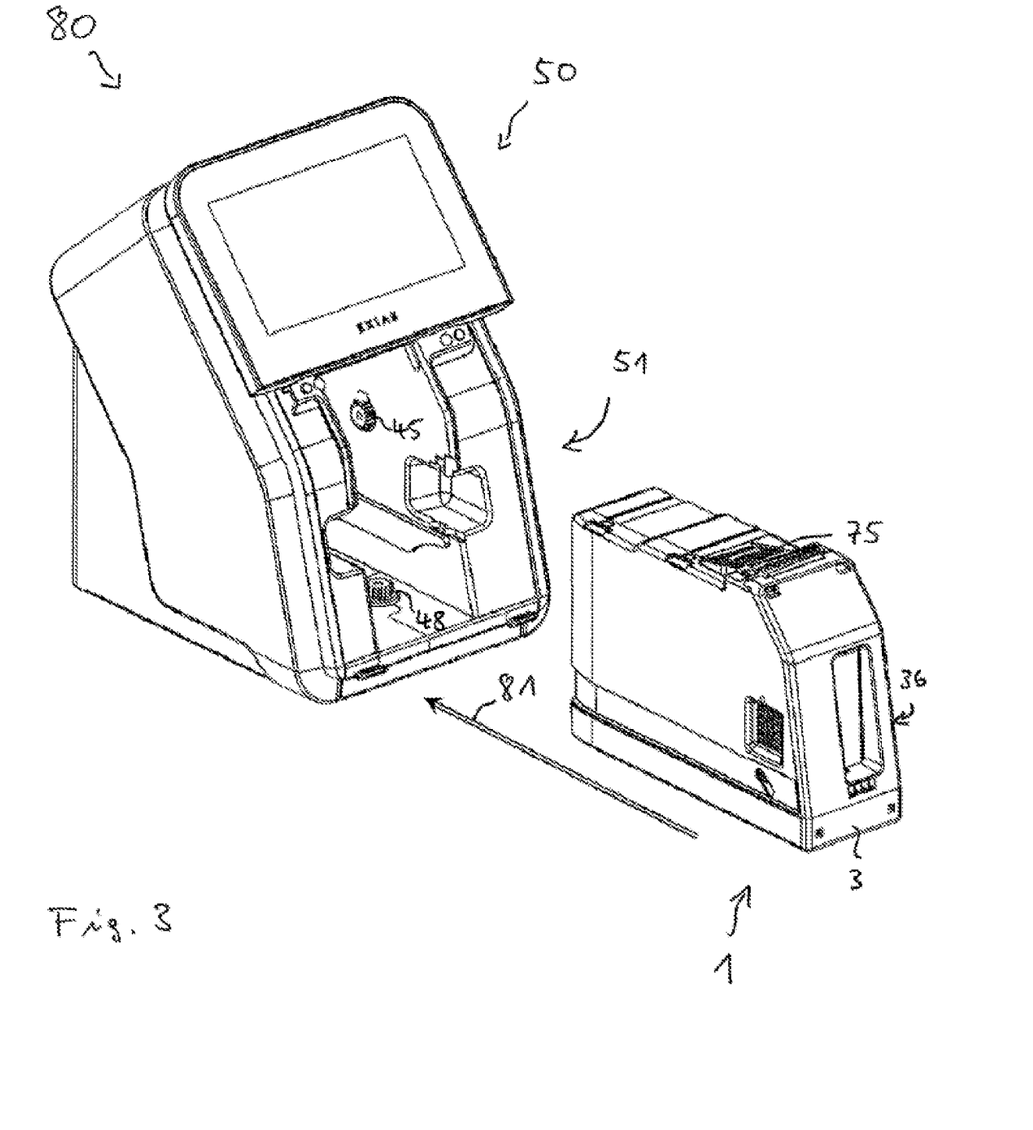
FIG. 3 schematically illustrates a measurement system according to an embodiment of the present invention comprising a measuring cartridge and a measuring instrument.

The supply needle 35 of the measurement cell 7 is straight and hollow having an inner lumen 39, wherein one end 41 of the supply needle 35 is reversibly connectable to the outlet 31 of the rotary distributor 19. In particular, the measurement cell 7 is a movable measurement cell which may be in particular rotated to change the orientation of the supply needle 35 for example to a configuration 35' as indicated with dashed lines in FIG. 1. For rotating the measurement cell 7, the measurement cell 7 comprises an engagement portion 43 for engaging with an only schematically illustrated gear wheel 45 which is not part of the measuring cartridge 1 but which is part of the measuring instrument 50 as illustrated in FIG. 3. The measuring instrument 50 comprises a reception opening 51 in which the measuring cartridge 1 is insertable, so that the gear wheel 45 which is accessible within the reception opening 51 is engaged with the engagement portion 43 of the measurement cell. The engagement portion 43 is further connected to a supporting portion 47 which is also connected to the measurement cell 7 which comprises a bar or a lever supporting the supply needle 35 at or close to the end 41. The gear wheel 45 for driving the measurement cell 7 is driven by for example an electric motor 46 being part of the measuring instrument 50.

The measurement cell can be moved, in particular translated, such that the supply needle 35 may be withdrawn from the outlet 31 of the rotary distributor 19 and the measurement cell 7 may then be rotated to reach a configuration as indicated with reference sign 35'. In the configuration 35', the supply needle may be configured or usable for loading a sample into the measurement cell, for example in a sample measurement mode.

In a quality control operation mode, the end 41 of the supply needle 35 is inserted into or at least connected with the outlet 31 of the rotary distributor 19 allowing to supply one of the control solutions 15a, 15b, 15c or a calibration solution to enter the measurement cell 7 for measurement. In the quality control operation mode, the selected quality control solution 15a, 15b, 15c contained within the respective quality control container 13a, 13b, 13c streams from the respective quality control container, in particular via a tubing or a respective hose 49, and via the respective inlet 21a, 21b, 21c of the rotary distributor 19, via the rotary distributor and via the supply needle 35 (inserted or connected with the outlet 31 of the rotary distributor 19) into the reception space 9 of the measurement cell. In particular, the selected quality control solution streams via the outlet 61 of the measurement cell out of the measurement cell in particular through a waste tube 63 to a waste container 65.

For causing solution flow, the waste tube 63 comprises a flexible portion 67 which is, when the measuring cartridge 1 is completely inserted into the measuring instrument 50, engaged or in contact with a driving wheel 69 of a peristaltic pump which is part of the measuring instrument 50. The driving wheel comprises plural pressing portions or rollers 71 which press against the flexible portion of the waste tube 67 in order to displace the fluid or liquid contained in the flexible waste tubing 67 when rotating in a direction indicated by the arrow 73. The peristaltic pump 68 is not part of the measuring cartridge 1 but is a part of the measuring instrument 50 illustrated in FIG. 3.

The measuring cartridge 1 further comprises plural electrical contact areas 75 which are accessible from outside the casing 3 and are adapted to at least electrically contact the sensor area 11 of the measurement cell 7 with a circuitry of the measuring instrument 50. Therefore, the measuring instrument 50 comprises corresponding electrical contact areas 77.

Figure 2:
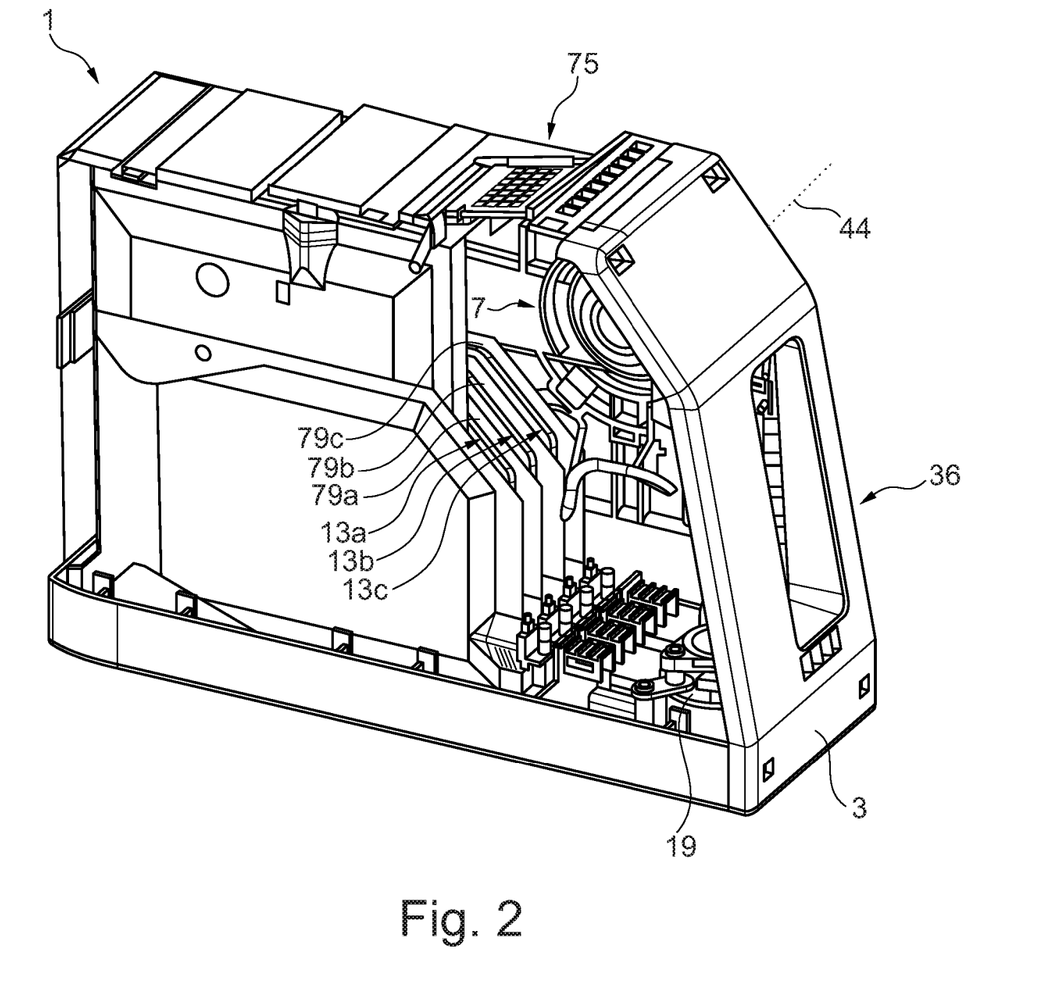
FIG. 2 schematically illustrates in a perspective view a measuring cartridge according to an embodiment of the present invention.

The measuring cartridge 1 schematically illustrated in FIG. 1 is depicted in a partially cut away three-dimensional view in FIG. 2 and is displayed in a three-dimensional view together with the measuring instrument 50 in FIG. 3.

As can be seen in FIG. 2, the quality control containers 13a, 13b, 13c are arranged side by side within receptacles 79a,b,c. At a lower end of the respective quality control containers 13a, 13b, 13c, a cap or a closure or a valve 50 may be provided to which the tubing is connected leading to the respective inlet of the rotary distributor 19.

The measurement cell 7 is arranged above the rotary distributor 19. Using the actuator 46, the gear wheel 45 may be rotated around a rotation axis 44 being in operation substantially oriented horizontally. By rotating the measurement cell 7, the supply needle 35 may be rotated to protrude from the measuring cartridge 1 through a sample supply opening 36 at a front face of the measuring cartridge 1. When the end 41 of the supply needle 35 at least partly protrudes out of the sample supply opening 36, a sample may easily be loaded into the measurement cell 7.

In FIG. 2, the electrical contact areas 75 are visible to be located on a top face of the measuring cartridge 1 so that the electrical contact areas are not in contact with any liquid.

FIG. 3 illustrates a measurement system 80 comprising the measuring instrument 50 and a measuring cartridge 1 which is for example illustrated in FIGS. 1 and 2. By translating the measuring cartridge along a straight direction 81, for example oriented substantially in the horizontal plane, the measuring cartridge 1 may be inserted into the reception opening 51 of the measuring instrument 50. The gear wheel 45 for rotating the measurement cell 7 is visible at a sidewall of the reception opening 51 and the gear wheel 48 for operating the rotary distributor 19 is visible at a bottom surface of the reception opening 51.

The system 80 is capable of performing a method for measuring at least one constituent of a liquid sample and for performing quality control according to an embodiment of the present invention. Thereby, the measuring cartridge 1 as inserted into the reception opening 51 of the measuring instrument 50 is utilized. A sample is loaded into the reception space 9 of the measurement cell 7 arranged within the inner space 5 of the measuring cartridge 1. At least one sensor area 11 of the measurement cell 7 is contacted with the sample. After having performed a particular number of sample measurements, a quality control operation mode may be adopted. During the quality control operation mode, one of the plural quality control solutions 15a, 15b, 15c is routed from a respective quality control container 13a, 13b, 13c within the inner space 5 of the measuring cartridge into the reception space 9 of the measurement cell 7.

A measurement result within the target range for analyte concentration may assure proper function of the system, whereas deviations may indicate a problem and may result in further measures, such as e.g. a calibration of measurement equipment or replacement of the measuring cartridge or measurement cell. The quality control solutions are contained in liquid tight bags or pouches and are directly integrated into the measuring cartridge. Thereby, the quality control may be performed directly by comparison the measurement values with target value ranges. Thereby, the quality control measurements may be automatically performed in the background, for example at the beginning of each working day or at regular time intervals. All components necessary for performing measurements of samples and quality control as well as calibration max be integrated into the measuring cartridge. The quality control solutions are guided via the normal sample path. Thereby, a minimal individual length of the supply path (for example smaller than 15 mm) may be achieved. Furthermore, a cost effective construction is achieved. Furthermore, ampules can be dispensed with, increasing the simplicity.

Embodiments of the present invention provide employment of one or more quality control solutions within a measuring cartridge with a sensor array for clinical parameters, wherein the quality control solutions are integrated with the other solutions required for normal operation or for calibration. The measurement may be performed in programmed procedures or in particular quality control workflows. The evaluation of the measuring values with respect to the target value ranges may be performed automatically. In particular, three different quality control liquids corresponding to three levels of relevant clinical ranges may be provided.

The invention claimed is:

1. A measuring cartridge for measuring at least one constituent of a liquid sample and for performing quality control, the cartridge comprising:
   a casing insertable into a reception opening of a measuring instrument, the casing at least partly surrounding an inner space;
   wherein the inner space contains:
   a measurement cell comprising a reception space for the sample and at least one sensor area with which the sample is in contact when loaded into the reception space;
   plural quality control containers for respectively holding different quality control solutions; and
   a solution routing system adapted to selectively route one of the quality control solutions from the respective quality control container into the reception space of the measurement cell, wherein the solution routing system comprises:
   a rotary distributor having plural inlets connected to at least the quality control containers and having at least one outlet engageable to an inlet of the measurement cell, the rotary distributor being adapted to allow solution communication between a selected inlet and the outlet.

2. The measuring cartridge according to claim 1, wherein the inlet of the measurement cell comprises a supply needle having an inner lumen, an end of the supply needle being reversibly connectable to the outlet of the rotary distributor.

3. The measuring cartridge according to claim 2, wherein the supply needle is straight and fixedly connected.

4. The measuring cartridge according to claim 2, wherein, in a quality control operation mode, the selected quality control solution streams from the respective quality control container via the solution routing system and via the supply needle into the reception space of the measurement cell and out of the measurement cell.

5. The measuring cartridge according to claim 2, wherein, in a quality control operation mode, the selected quality control solution streams from the respective quality control container via the rotary distributor and via the supply needle into the reception space of the measurement cell and out of the measurement cell.

6. The measuring cartridge according to claim 2, wherein the measurement cell comprises an engagement portion for engaging with a gear wheel accessible in the reception opening of the measuring instrument when the measuring cartridge is inserted into the reception opening, allowing to move the measurement cell, allowing to remove the supply needle from the outlet of the rotary distributor and to expose the end of the needle through a sample supply opening within the casing of the cartridge for loading a sample to be examined.

7. The measuring cartridge according to claim 1, further comprising:
   at least one calibration container for holding a calibration solution for calibrating the sensor area of the measurement cell, the calibration container being connected to the rotary distributor.

8. The measuring cartridge according to claim 1, wherein the different quality control solutions contain mixtures of plural target constituents in different concentrations.

9. The measuring cartridge according to claim 8, wherein the plural target constituents include at least one of: H+, Na+, K+, $Ca^{2+}$, $Cl^{2-}$.

10. The measuring cartridge according to claim 8, wherein the different concentrations of the plural target constituents within the different quality control containers are selected to at least correspond to a physiologically normal range, to a pathologically elevated range, and to a pathologically lowered range.

11. The measuring cartridge according to claim 1, wherein at least one of the plural quality control containers comprises a pouch made of a laminate.

12. The measuring cartridge according to claim 11, wherein the laminate comprises at least an aluminum foil covered by or glued together with a synthetic foil which is in contact with the respective quality control solution.

13. The measuring cartridge according to claim 1, wherein at least one of the plural quality control containers has a volumetric capacity of between 1 ml and 100 ml.

14. The measuring cartridge according to claim 1, wherein the plural quality control containers are arranged side by side within receptacles within the inner space.

15. The measuring cartridge according to claim 1, further comprising:
   plural electrical contact areas accessible from outside the casing adapted to at least electrically contact the sensor area of the measuring cell with circuitry of the measuring instrument.

16. A measuring system, comprising:
   a measuring instrument having a reception opening; and
   a measuring cartridge according to claim 1 insertable into the reception opening, the measuring instrument being adapted to receive measurement signals from the sensor of the measurement cell, the measuring instrument being adapted to selectively:
   adopt a quality control operation mode, in which a quality control solution from one of the quality control containers is supplied into the reception space of the measurement cell; or
   adopt a sample measurement mode, in which a sample is supplied into the reception space of the measurement cell.

17. A method for measuring at least one constituent of a liquid sample and performing quality control, the method comprising:
   using a measuring cartridge with a casing inserted into a reception opening of a measuring instrument, the casing at least partly surrounding an inner space;
   loading a sample into a reception space of a measurement cell arranged within the inner space;
   contacting at least one sensor area of the measurement cell with the sample; and
   routing, using a rotary distributor one of plural quality control solutions from a respective quality control container arranged within the inner space into the reception space of the measurement cell,
   the rotary distributor having plural inlets connected to at least the quality control containers and having at least one outlet engageable to an inlet of the measurement cell, the rotary distributor being adapted to allow solution communication between a selected inlet and the outlet.

18. The method according to claim 17, further comprising at least one of:
   measuring one of the plural quality control solutions within the measurement cell to generate quality control measurement results;
   comparing quality control measurement results with at least one reference value associated with the one of the plural quality control solutions; and
   retrieving a history of quality control measurement results.

19. The method according to claim 18, further comprising:
   storing the quality control measurement results.

* * * * *

UNITED STATES PATENT AND TRADEMARK OFFICE
CERTIFICATE OF CORRECTION

PATENT NO. : 11,536,711 B2
APPLICATION NO. : 16/665868
DATED : December 27, 2022
INVENTOR(S) : Wolfgang Hofmann et al.

It is certified that error appears in the above-identified patent and that said Letters Patent is hereby corrected as shown below:

In the Drawings
FIG. 1, Sheet 1 of 3, Line 1, and on the title page, the illustrative print figure Delete "3 ponches", insert --3 pouches--, as shown on the attached Drawing Sheet 1

In the Claims
Column 15, Lines 11-12, Claim 9

Delete "H+, Na+, K+," and insert --$H^+$, $Na^+$, $K^+$,--

Signed and Sealed this
Eleventh Day of April, 2023

Katherine Kelly Vidal
*Director of the United States Patent and Trademark Office*